United States Patent
Harding et al.

(12) 
(10) Patent No.: US 6,678,057 B2
(45) Date of Patent: Jan. 13, 2004

(54) METHOD AND DEVICE FOR REDUCTION IN NOISE IN IMAGES FROM SHINY PARTS

(75) Inventors: Kevin George Harding, Niskayuna, NY (US); Thomas Watkins Lloyd, Shrewsbury, VT (US); Joseph Benjamin Ross, Cincinnati, OH (US)

(73) Assignee: General Electric Company, Niskayuna, NY (US)

( * ) Notice: Subject to any disclaimer, the term of this patent is extended or adjusted under 35 U.S.C. 154(b) by 105 days.

(21) Appl. No.: 09/683,365

(22) Filed: Dec. 19, 2001

(65) Prior Publication Data

US 2003/0112447 A1 Jun. 19, 2003

(51) Int. Cl.[7] .............................. G01B 11/24; G01J 4/00
(52) U.S. Cl. ........................................ 356/603; 356/369
(58) Field of Search ................................ 356/602, 603, 356/604, 612, 364, 369, 370

(56) References Cited

U.S. PATENT DOCUMENTS

| | | | | |
|---|---|---|---|---|
| 4,842,411 A | * | 6/1989 | Wood | 356/603 |
| 5,428,448 A | * | 6/1995 | Albert-Garcia | 356/612 |
| 5,589,942 A | | 12/1996 | Gordon | 356/376 |
| 6,028,671 A | * | 2/2000 | Svetkoff et al. | 356/368 |
| 6,128,085 A | * | 10/2000 | Buermann et al. | 356/369 |
| 6,437,856 B1 | * | 8/2002 | Jacques | 356/39 |
| 6,549,288 B1 | * | 4/2003 | Migdal et al. | 356/603 |
| 2002/0196438 A1 | * | 12/2002 | Kerschbaumer et al. | 356/327 |

OTHER PUBLICATIONS

B. Liang, A.M. Wallace, and E. Trucco, "Measurement Errors In Polarization–Based 3D Vision Systems", SPIE Proceedings vol. 2909, Three–Dimensional Imaging and Laser Based Systems for Metrology and Inspection ii, editor Harding, Boston, Nov. 1996, pp. 204–214.

* cited by examiner

Primary Examiner—Alan A. Mathews
(74) Attorney, Agent, or Firm—Jean K. Testa; Patrick K. Patnode

(57) ABSTRACT

A method for filtering undesired light reflections in a structured light measurement system during the inspection of shiny metal prismatic objects having uncoated prismatic surfaces, such as turbine blades, using polarized light.

10 Claims, 1 Drawing Sheet

METHOD AND DEVICE FOR REDUCTION IN NOISE IN IMAGES FROM SHINY PARTS

BACKGROUND OF INVENTION

The present invention provides a method for reducing noise in a non-contact gauge measurement system utilizing structured light. In particular, the present invention provides a method to facilitate inspection of prismatic objects having uncoated surfaces, such as turbine or compressor blades, using a combination of object orientation and polarized light in an optical three-dimensional structured light gauge measurement system.

Traditionally, gauge measurement of a manufactured object having a complex three dimensional surface such as an airfoil (e.g. compressor blade) is a tedious and time consuming process. Airfoils, including forged blades such as those used on aircraft engines, electrical power generators, and the like, are inspected for deformations which may include, but are not limited to, skew, twist, scaling, and translation. More specifically, airfoils are inspected for deformation parameters such as platform orientation, contour cross-section, bow and twist along a stacking axis, thickness, and chord length at given cross-sections.

One method of obtaining dense and accurate digital data representing these parameters for an individual airfoil is through use of a coordinate measuring machine (commonly known as a "CMM"). CMM's translate and rotate a sensor probe into contact with the surface of an object undergoing testing to sample the position of various points on the object's surface. Before a sensor probe may be brought into contact with an object, the object must be secured in a known physical position and orientation, such that a set of known reference points may be established. For airfoil measurement, six physical contact points are utilized, defining a "six point nest". This set of six data points establish the position and orientation of the airfoil in its physical holder and enable the contact points to be translated to any other coordinate system. CMM's provide high quality (i.e. highly accurate) measurements of the sample points. However, the time to scan an airfoil is relatively slow as the process of positioning the airfoil in the six point nest is time-consuming, and the sensor probe must be continually repositioned to obtain data. Once the high quality surface points are collected, software processes these points into deviations from values generated in a computer assisted drawing (CAD) model of the object and analyzes the deviations in terms of process-based shape deformations. Current CMM processing software, however, is also relatively slow.

An alternate method of obtaining measurements representing deformation parameters of an object employs full-field non-contact range sensors. Non-contact full-field sensors can quickly scan the external surfaces of opaque objects, using laser or white light, significantly faster than CMMs. Examples of non-contact sensors include sensors that project laser line gratings onto the surface of an object and process detected images thereof using stereo triangulation; and those based on single laser line scan plus rotation of the object. Additional non-contact sensors are based on phase-shifted moir é patterns and white light. While these sensors are capable of scanning the part quickly and obtaining large quantities of data, the level of accuracy is affected by undesirable reflections of the scan light from shiny or prismatic surfaces on the object.

To compensate for these undesired reflections, shiny or prismatic surfaces on the object are traditionally coated with a diffusing material such as a paint or powder to non-contact gauge measurement. This additional step adds uncertainty to the measurement, and increases measurement time which is highly undesirable. Accordingly, there is a need for eliminating or reducing the effect of undesired reflections from shiny or prismatic object surfaces in a non-contact measurement system in a manner which does not require application of diffuse coatings to surfaces of the object being tested.

SUMMARY OF INVENTION

Briefly stated, the present invention provides a method for the inspection of shiny metal prismatic objects having uncoated prismatic surfaces, such as compressor blades, using polarized light in an optical three-dimensional structured light measurement system.

In one embodiment of the present invention, a structured light measurement system projects a structured light pattern onto the surface of an object, parallel to a plane bisecting one or more prismatic features of the object. An imaging system receives the structured light pattern reflected from the surface of the object and analyzes the deformation of the reflected light pattern to calculate the surface features of the object. The projected light is polarized at a known polarization angle, and the reflected light is polarized to a related angle, such that light reflected directly and indirectly from the planar surfaces of the object is separated by the imaging system. Using multiple images of the object obtained with polarized light, difference images and region masks can be generated to reduce or eliminate undesired reflections and noise from the resulting images of the object.

The foregoing and other objects, features, and advantages of the invention as well as presently preferred embodiments thereof will become more apparent from the reading of the following description in connection with the accompanying drawings.

BRIEF DESCRIPTION OF DRAWINGS

In the accompanying drawings which form part of the specification.

Corresponding reference numerals indicate corresponding parts throughout the several figures of the drawings.

DETAILED DESCRIPTION

The following detailed description illustrates the invention by way of example and not by way of limitation. The description clearly enables one skilled in the art to make and use the invention, describes several embodiments, adaptations, variations, alternatives, and uses of the invention, including what is presently believed to be the best mode of carrying out the invention.

Figure 1:
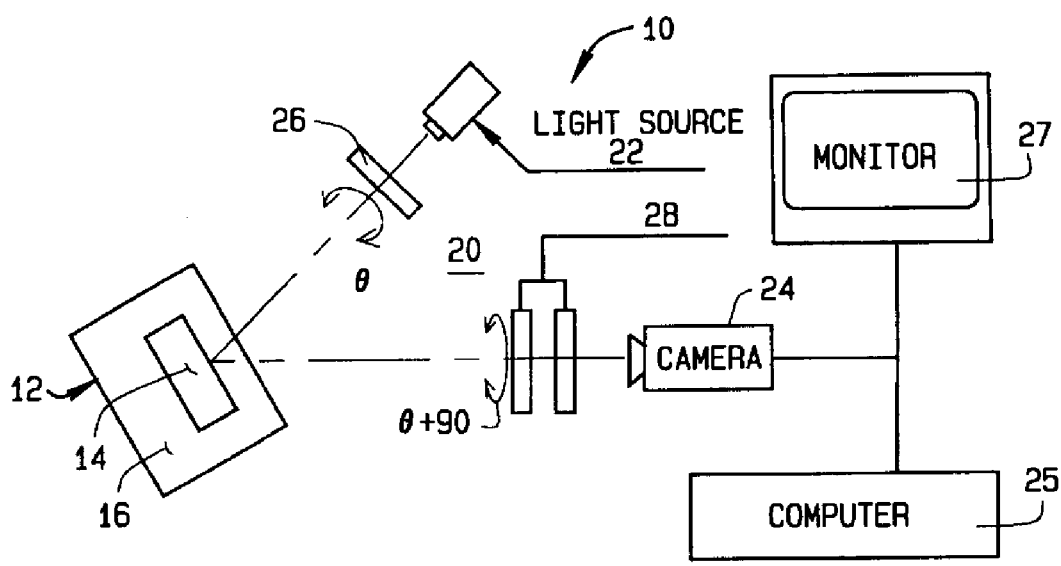
FIG. 1 is a block diagram of an apparatus for effecting the method of the present invention for measuring surface features of an object under test.

FIG. 1 is a block diagram of an apparatus 10 for measuring surface features of a manufactured object 12, according to one embodiment of the present invention. Apparatus 10 is adapted to inspect and determine surfaces of the object. These surfaces may include features such as tilts, bends, twists, or warps when compared to a reference model or other ideal representations of the object.

In one embodiment of the invention, object 12 comprises a blade, e.g., a compressor blade of an aircraft engine, having an airfoil 14 extending from a platform 16, and having an axis 18. While the following description is directed to inspecting blades, one skilled in the art will appreciate that the apparatus and the method of the present invention may be utilized to improve structured light imaging for any object having similar characteristics.

An object 12 to be inspected is positioned within the sensing range of an imaging system 20, preferably a full field, non-contact, laser line grating range sensor mounted on a translation stage. The imaging system comprises a structured light emitter 22 and one or more imaging sensors 24 configured to receive structured light reflected from object 12. One or more computers 25 are utilized to process images received from the sensors 24, and a monitor 27 may be utilized to display information to an operator.

Full field, non-contact range sensors suitable for use as imaging systems 20 are currently readily available from commercial sources. For example, the model 4DI sensors sold by Integrated Automation Systems may be employed with the present invention. The 4DI sensors utilize the projection of a laser line grating onto the surface on an object 12, and the stereo triangulation of the projected lines by one or more imaging detectors. Other suitable sensors employ single laser line scans with rotation of the object, or phase-shifted Moiré and white light.

Figure 2:
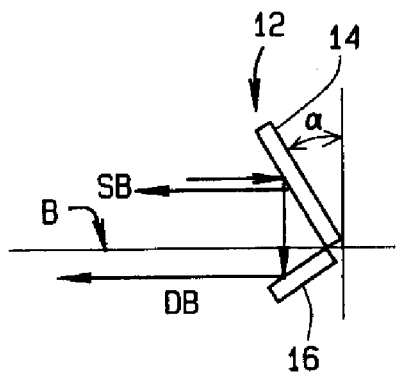
FIG. 2 is a side sectional view of an object under test, illustrating single-bounce and double-bounce light paths.

To improve the performance of the full-field, non-contact range sensors on objects 12 having shiny or prismatic surfaces, the object is positioned in a preferred orientation relative to the source of structured light. As seen in FIG. 2, the angle α of orientation is selected so as to present a view to the imaging sensors 24 in which a plane β defined by light emitter 22 and imaging sensors 24 approximately bisect one or more prismatic features on the surface of the object 12. For example, if the object 12 comprises a compressor blade, airfoil 14 and platform 16 define a prismatic feature of the blade, as a portion of light projected onto the airfoil may reflect onto platform 16, thus producing a double reflection back towards the imaging system 20.

To reduce and identify reflections of the projected light from prismatic features of object 12, the structured light projected onto the surface of the object from light emitter 22 is polarized with a polarizing filter 26 oriented at a known angle θ relative to a the plane β defined by light emitter 22 and imaging system 20. A second polarizing filter 28 is placed between imaging sensors 24 and object 12 and oriented to block any light reflected back through two surface reflections. Now, any light reflecting off two facets of the prismatic surfaces of the object is reduced in intensity or completely blocked from the imaging sensors.

The imaging sensors 24 obtain an image of the structured light. projected onto a surface of object 12. This image is composed of an array of pixels, with each pixel representing the intensity of received light at that particular point in the image. If some portions of the image are either over or under saturated, i.e. the intensity levels exceed a maximum observable level or does not reach a minimum threshold level, additional images of the object can be taken with the structured light projected at different levels of intensity and/or with different polarization angles so to provide additional data in the usual manner.

Only directly reflected light from a surface of object 12 can be readily interpreted in a structured light imaging system 20. A directly reflected light path is indicated as SB in FIG. 2. Light which has reflected off of a prismatic surface on the object, as indicated by light path DB in FIG. 2,(i.e. "double-bounce light"), produces light patterns observed by the imaging sensors 24, but at erroneous orientations. This can lead to an incorrect interpretation of the surface features of object 12.

Figure 3:
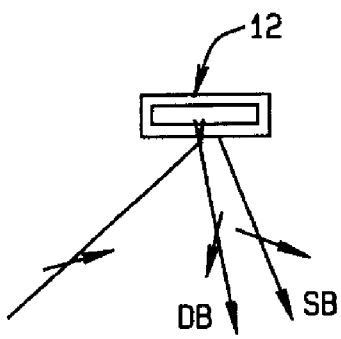
FIG. 3 is a top view of an object under test, illustrating changes in reflected light polarization for light following the paths shown in FIG. 2.

As shown in FIG. 3, the polarization of any light which has bounced off of two or more surfaces of object 12 is changed so as to be different from directly reflected light. By selecting polarization angle θ for the light illuminating the surface of object 12, and subsequent filtering of the light as seen by the imaging sensors 24, single bounce and double bounce light is effectively separated.

Reflected light which has bounced off of two prismatic surfaces of object 12 is enhanced by positioning the second polarization filter 28 in front of imaging sensor 24 so to be 90° out of phase with the first polarization filter 26 which is placed in front of the structured light emitters 22. Other orientations of the second polarization filter 28 can provide additional information on the angle and number of bounces through which light received by the imaging sensor 24 has passed.

By taking multiple images of the structured light projected on a surface of object 12, and using different polarizations angles of second polarization filter 28, reflections from single bounce light, double bounced light, or other variations, are readily identified and selectively extracted from the image using conventional image processing techniques.

Suitable image processing methods include subtraction or difference imaging between two images, masking of certain areas of an image, as well as correlations of image information. For example, it is known that if two or more images of an object are obtained, and are correlated such that they have common reference points or are from the same position and orientation, digital processing techniques permit one image to be "subtracted" from the other, so to obtaining a resulting difference image. This resulting difference image includes only information on those regions in the field of view which have changed between the first and second images.

Alternatively, with prior knowledge of the shape or configuration of the object undergoing measurement, or two or more images, specific regions in an image known to contain erroneous or irrelevant information may be digitally masked or blocked from further processing. For example, using subtraction techniques, regions of an image containing background can be identified in a difference image, and then utilized to mask out background regions in subsequent or current or subsequent images.

Similarly, using known information or multiple images, an image of an object undergoing measurement may be correlated or registered to a stored reference image, facilitating identification of differences between the object and an ideal model or representation of the object.

In this manner, even if the second polarizing lens 28 does not completely block unwanted light reflections from imaging sensor 24, the effects of the these reflections can be analyzed within the image and incorrect information sorted from correct information for use in the surface inspection of the object.

In view of the above, it will be seen that the several objects of the invention are achieved and other advantageous results are obtained. As various changes could be made in the above constructions without departing from the scope of the invention, it is intended that all matter contained in the above description or shown in the accompanying drawings shall be interpreted as illustrative and not in a limiting sense.

What is claimed is:

1. A method for reducing noise in a structured light measurement system having a structured light emitter projecting structured light onto a surface of an object, and an imaging system receiving structured light reflected from the surface of the object, comprising:

polarizing said projected structured light at a known polarization angle;

polarizing said reflected structured light at said known polarization angle wherein projected structured light reflected indirectly from the surface of the object is filtered from said imaging system;

obtaining a first image of said polarized reflected structured light with said imaging system;

obtaining a second image of said polarized reflected structured light with said imaging system; and, comparing said first image and said second image of said polarized reflected structured light to identify surface features of the object and wherein comparing said first image and said second image includes masking regions within said first image.

2. The method of claim 1 further including using a second polarizing filter for polarizing said reflected structured light at a second polarization angle oriented 90° relative to said known polarization angle whereby the projected structured light reflected directly from the surface of the object is filtered from said imaging system.

3. The method of claim 1 wherein comparing said first image and said second image includes generation of a difference image identifying distinctions between said first image and said second image.

4. The method of claim 1 further including orienting the object at an angle selected to facilitate the filtering of projected structured light reflected indirectly from the surface of the object from said imaging system.

5. The method of claim 4 wherein the object is orientated at an angle selected to bisect one or more prismatic features of the object.

6. A method for reducing noise in a structured light measurement system having a structured light emitter for projecting structured light onto the surface of an object having at least one prismatic feature, and an imaging system for receiving structured light reflected from a surface of the object, the structured light emitter and imaging system defining a plane, the method comprising:

orienting the object in a field of view of said imaging system, such that said at least one prismatic feature is bisected by said plane;

polarizing said projected structured light at a known polarization angle relative to said plane;

polarizing said reflected structured light at said known polarization angle relative to said plane, wherein projected structured light reflected indirectly from the surface of said object is filtered from said imaging system; and obtaining an image of said polarized reflected structured light with said imaging system.

7. The method of claim 6 further including using a second polarizing filter for polarizing said reflected structured light at a second polarization angle relative to said known polarization angle, wherein a portion of said projected structured light reflected from the surface of said object is filtered from said imaging system; and obtaining a second image of said polarized reflected structured light with said imaging system.

8. The method of claim 7 further including comparing said first image and said second image of said polarized reflected structured light to identify surface features of the object.

9. A method for reducing noise in a structured light measurement system having a structured light emitter for projecting structured light onto a surface of an object, and an imaging system for receiving structured light reflected from the surface of the object, comprising:

orienting said object at a selected orientation to present a view of said surface to said imaging system;

polarizing said projected structured light at a known polarization angle;

polarizing said reflected structured light at said known polarization angle;

obtaining an image of said polarized reflected structured light with said imaging system; and wherein said selected orientation and said known polarization angle cooperate to filter said projected structured light reflected indirectly from the surface of said object from said imaging system.

10. The method of claim 9 for reducing noise in a structured light measurement system wherein said selected orientation is selected to present a view to said imaging system bisecting at least one prismatic feature on the surface of the object.

* * * * *